US010806606B2

(12) United States Patent
Alley

(10) Patent No.: US 10,806,606 B2
(45) Date of Patent: Oct. 20, 2020

(54) SKELETAL STABILIZATION LINER SYSTEM

(71) Applicant: Randall D. Alley, Thousand Oaks, CA (US)

(72) Inventor: Randall D. Alley, Thousand Oaks, CA (US)

( * ) Notice: Subject to any disclaimer, the term of this patent is extended or adjusted under 35 U.S.C. 154(b) by 199 days.

(21) Appl. No.: 15/019,683

(22) Filed: Feb. 9, 2016

(65) Prior Publication Data
US 2016/0228266 A1 Aug. 11, 2016

Related U.S. Application Data

(60) Provisional application No. 62/115,142, filed on Feb. 11, 2015.

(51) Int. Cl.
A61F 2/80 (2006.01)
A61F 2/50 (2006.01)
A61F 2/78 (2006.01)

(52) U.S. Cl.
CPC .............. A61F 2/80 (2013.01); A61F 2/5044 (2013.01); A61F 2/7812 (2013.01); A61F 2/7843 (2013.01); A61F 2002/785 (2013.01); A61F 2240/001 (2013.01)

(58) Field of Classification Search
CPC .............. A61F 2/7812; A61F 2002/785; A61F 2002/023; A61F 2002/5055
See application file for complete search history.

(56) References Cited

U.S. PATENT DOCUMENTS

| 1,144,681 | A |   | 6/1915  | Apgar |
| 1,272,179 | A |   | 7/1918  | Anderson |
| 2,229,728 | A |   | 1/1941  | Eddels |
| 2,506,464 | A |   | 5/1950  | Millheisler |
| 2,749,914 | A | * | 6/1956  | Braley ............. A61F 7/02 607/112 |
| 3,111,683 | A |   | 11/1963 | Bach |
| 4,128,903 | A |   | 12/1978 | Marsh et al. |

(Continued)

FOREIGN PATENT DOCUMENTS

| ES | 2157778 A1 | 4/1999 |
| FR | 2539616 A1 | 7/1984 |

(Continued)

OTHER PUBLICATIONS

PI01091EP1 Extended European Search Report, dated Aug. 1, 2016.

(Continued)

Primary Examiner — Bruce E Snow
Assistant Examiner — Melissa A Hoban
(74) Attorney, Agent, or Firm — Fish IP Law, LLP

(57) ABSTRACT

A liner with at least three substantially equally spaced attachment areas arranged longitudinally from the proximal to the distal end of the liner so as to permit relief areas between attachment areas and increase the radial thickness of the liner in the area of the liner inherently or through the addition of shims or other materials at the attachment areas. The liner and shims can be selected from a kit of different shaped liners and shims. Methods for making such a liner or liners for a kit. A method for iteratively attaching shims to the liner to prevent substantial movement of a limb's skeletal structure when the liner is worn with a socket.

35 Claims, 11 Drawing Sheets

(56) References Cited

U.S. PATENT DOCUMENTS

| | | |
|---|---|---|
| 4,459,709 A | 7/1984 | Leal |
| 4,921,502 A | 5/1990 | Shamp |
| 5,101,815 A | 4/1992 | Langdon-Orr et al. |
| 1,893,853 A | 1/1993 | Tullis |
| 5,246,464 A | 9/1993 | Sabolich |
| 5,258,037 A * | 11/1993 | Caspers ............... A61F 2/5046 623/33 |
| 5,288,286 A | 2/1994 | Davis |
| 5,405,405 A | 4/1995 | Love |
| 5,507,836 A | 4/1996 | Pohlig |
| 5,718,925 A | 2/1998 | Kristinsson et al. |
| 5,724,714 A | 3/1998 | Love |
| 5,728,167 A | 3/1998 | Lohmann |
| 5,830,237 A | 11/1998 | Kania |
| 5,888,230 A | 3/1999 | Helmy |
| 5,931,872 A | 8/1999 | Lohmann |
| 5,972,036 A | 10/1999 | Kristinsson et al. |
| 6,077,300 A | 6/2000 | Sabolich et al. |
| D429,335 S | 8/2000 | Caspers et al. |
| 6,362,387 B1 | 3/2002 | Carlson et al. |
| 6,482,238 B1 | 11/2002 | Grundei |
| 6,712,780 B2 | 3/2004 | Darcey |
| 6,994,732 B2 | 1/2006 | Price, Jr. |
| 7,291,182 B1 | 11/2007 | Kania |
| 7,377,944 B2 | 5/2008 | Janusson |
| 8,323,353 B1 | 12/2012 | Alley et al. |
| 8,409,298 B2 | 4/2013 | Perkins |
| 8,443,501 B2 | 5/2013 | Mahon |
| 8,523,951 B2 | 9/2013 | Kania |
| 8,656,918 B1 | 2/2014 | Alley et al. |
| 8,795,386 B2 | 8/2014 | Pianykh et al. |
| 8,828,094 B2 | 9/2014 | Halldorsson |
| 9,283,093 B2 | 3/2016 | Alley |
| 2003/0181989 A1* | 9/2003 | Eberle ............... A61F 2/5046 623/36 |
| 2004/0049141 A1 | 3/2004 | Slautterback et al. |
| 2004/0158332 A1 | 8/2004 | Carstens |
| 2005/0267599 A1 | 12/2005 | Bjarnason |
| 2007/0061017 A1 | 3/2007 | Wilson |
| 2007/0162153 A1 | 7/2007 | Barnes et al. |
| 2010/0042227 A1 | 2/2010 | Schmidt |
| 2010/0082116 A1 | 4/2010 | Johnson et al. |
| 2010/0274364 A1 | 10/2010 | Pancanowsky et al. |
| 2011/0118853 A1 | 5/2011 | Kim |
| 2011/0247321 A1 | 10/2011 | Streeter et al. |
| 2012/0101597 A1 | 4/2012 | Bache |
| 2012/0271433 A1* | 10/2012 | Galea ............... A61F 2/7812 623/37 |
| 2013/0053981 A1 | 2/2013 | Alley |
| 2013/0123940 A1 | 5/2013 | Hurley |
| 2013/0218296 A1 | 8/2013 | Koniuk et al. |
| 2013/0245789 A1* | 9/2013 | Iimura ............... B25B 21/00 700/12 |
| 2014/0005798 A1 | 1/2014 | Bache |
| 2014/0277584 A1 | 9/2014 | Hurley et al. |
| 2017/0065442 A1 | 3/2017 | Alley |
| 2017/0156896 A1 | 6/2017 | Alley |

FOREIGN PATENT DOCUMENTS

| | | | |
|---|---|---|---|
| FR | 2828093 | A1 | 2/2007 |
| GB | 127451 | A1 | 6/1918 |
| NO | 9503760 | A1 | 12/1995 |
| WO | 2012167384 | | 12/2012 |
| WO | 2014130878 | | 8/2014 |

OTHER PUBLICATIONS

Charles G. Hutter, MD, "A Suction Socket Prosthesis Without Suction," article, Orthopedic & Prosthetic Appliance Journal, Sep. 1957 (5 pages).

R. Volkert, "Frame type socket for lower limb prostheses," article, Prosthetics and Orthotics International, 1982, 6, 88-92.

Decision on Appeal, dated Mar. 21, 2017, U.S. Appl. No. 12/663,282.

Alley, U.S. Appl. No. 15/258,727, filed Feb. 23, 2017.

Examiner's Answer dated Sep. 23, 2016, U.S. Appl. No. 13/663,282.

Decision on Request for Rehearing, dated Jun. 2, 2017, U.S. Appl. No. 13/663,282.

Office Action dated Aug. 11, 2017, U.S. Appl. No. 14/156,962.

Jalleytwo. High-Fidelity Prosthetic Socket. Post date: Jun. 10, 2011. http://www.youtube.com/watch?v=NBNV7d46rQ4.

Ohio Willow Wood Liners. http:/fwww.willowwoodco.com/products-and-services/liners Verified by the wayback machine Mar. 26, 2011.

ISA/KR, Notification of Transmittal of the International Search Report and the Written Opinion of the International Searching Authority, or the Declaration, dated Feb. 6, 2014, PCT/US2013/067085.

ISA/KR, Written Opinion of the International Searching Authority, dated Feb. 6, 2014, PCT/US2013/067085.

ISA/KR, International Search Report, dated Feb. 6, 2014, PCT/US2013/067085.

Randall D Alley, "Prosthetic sockets stabilized by alternating areas of tissue compression and release," Journal of Rehabilitation Research & Development, vol. 48 No. 6, 2011, pp. 679-696.

"Biodesigns Inc Maximizing Human Performance", advertisement, inMotion Magazine, Apr. 2008 (1 page).

Randall Alley, "New Interface Design Benefits the High Performance Individual", article, Challenge Magazine, Jun. 2008 (1 page).

Pre-Brief Appeal Conference decision dated Mar. 22, 2016, U.S. Appl. No. 13/663,282.

Declaration of Randall D. Alley, executed Jun. 29, 2012.

Declaration of Randall D. Alley of Aug. 2013, executed Aug. 14, 2013.

"RCR Transtibial Socket", web page from www.coyotedesign.com, printed Dec. 11, 2002 (1 pg.).

ISA/KR, Notification of Transmittal of the International Search Report and the Written Opinion of the International Searching Authority, or the Declaration, dated Jun. 15, 2016, PCT/US2016/017178.

ISA/KR, Written Opinion of the International Searching Authority, dated Jun. 15, 2016, PCT/US2016/017178.

ISA/KR, International Search Report, dated Jun. 15, 2016 PCT/US2016/017178.

Alley, U.S. Appl. No. 15/258,727, filed Sep. 7, 2016.

EP Search Report dated Aug. 30, 2018 for EP Application16749727.0 entitled Skeletal Stabilization Liner System based on PCT/US2016/017178 in the name of Randall A. Alley.

* cited by examiner

SKELETAL STABILIZATION LINER SYSTEM

CROSS REFERENCE TO RELATED APPLICATIONS

This application claims the benefit of priority from U.S. Provisional Patent Application No. 62/115,142, filed Feb. 11, 2015, all of which application is incorporated in its entirety by reference herein.

BACKGROUND OF THE INVENTION

Traditional sockets utilize essentially a peripheral control scheme, wherein prosthetic device control results from global volume reduction and pressure on the entire residual limb. A compression stabilized socket or HiFi™ Socket made by biodesigns, inc., applies significantly more compression than could be done utilizing a global compression model and does so in biomechanically optimized zones or target areas with alternating tissue release zones in order to limit bone motion.

A target area and the synonymous term, "area of compression," refer to an area of a residual limb selected by a clinician for compression as disclosed in U.S. Pat. No. 8,656,918 and U.S. Pat. Application No. 20140121783, which are incorporated herein in their entirety by this reference.

A target area is defined by an area of compression parallel to the long axis of the major bone or bones of the residual anatomy, running virtually the entire length of the bone in the residual limb, ending just short of the bone ends, however, a shorter target area can be selected in particular applications. In circumstances where the length of the bone in the residual limb is substantially shorter than the length of the residual limb, a target area is selected so that it runs beyond the length of the bone in the residual limb in order to apply compression to tissue beyond the bone ends to supplement the association between the physical movement of the bone and the resulting movement of the socket by also capturing the motion of the tissue beyond the bone ends.

The outside perimeters of such a target area are defined by the need to provide open or low-compression relief areas outside the area of compression so that the compression is not impeded by the inability of the underlying tissue to flow or migrate sideways away from the shafts of the aforementioned bone or bones (or away from the compression ends at the proximal and distal ends of the compression areas). Selection of a target area takes advantage of the anatomical response such that tissue can be compressed against bone just so far before further motion is impeded, if there is room for the displaced tissue to move out of the way. By this process, the clinician is able to establish optimal tissue compression, which is a compression force against soft tissue overlying skeletal structure such that lost motion between the compression stabilized socket and the underlying skeletal structures is minimized without causing discomfort to the wearer for a usable amount of time. Optimal tissue compression also describes the supplemental compression force desired when target areas extend beyond the length of the bone for applications where the length of the bone in the residual limb is substantially shorter than the length of the residual limb.

Lost motion can be understood with reference to traditional sockets. In traditional sockets, lost motion occurs when force is applied between the socket wall and the underlying skeletal structures of the wearer, as would occur as an amputee tries to move the prosthesis as a whole. Lost motion occurs when the bone moves towards the socket wall a substantial distance before imparting force to the wall, causing a degree of disassociation between the physical movements of the body part in the socket and the resulting movement of the socket and attached prosthetic.

A "usable amount of time" is the amount of time a clinician or wearer expects the wearer to wear a socket on a typical day or for a planned activity.

Despite its advantages, a compression stabilized socket is more costly to produce than a traditional socket because it requires specialized training and equipment, and substantial time and labor to create. In addition, the wearer's residual limb may lose volume after the compression stabilized socket is fitted, reducing the compression and bone control achieved by that socket.

There are many different prosthetic liners used with sockets. Some liners add material of the same or different durometer to the liner during its fabrication (called a custom liner) to increase the liners thickness, but every known example cites comfort as the main reason for doing so, or the desire to make tissue contact, for example, in a heavily invaginated scar area, rather than bone control. As such, the number of thickened areas and their location on these liners are not optimized for bone control.

SUMMARY OF THE INVENTION

The Skeletal Stabilization Liner System ("SSLS") improves the underlying bone control in a traditional socket, which a wearer may have chosen because a compression stabilized socket is too costly, or where a wearer prefers a traditional socket design, by allowing clinicians to simply order and fit or retrofit a liner using the principles of the invention. In this manner, the clinician is able to achieve somewhat similar results to the use of a compression stabilized socket, even when a traditional socket is used, although the level of bone control may not completely match the level of bone control that can be achieved with a compression stabilized socket. The SSLS also allows the wearer of a compression stabilized socket to adjust the compression of the socket to account for loss of residual limb volume after fitting.

Unlike liners previously known, the SSLS is designed to minimize bone motion using an external pocket or other attachment area at a target area with which to affix a shim to the liner and increase the liner's radial width at the attachment area, which in turn causes the liner to compress underlying bone when the liner is donned and used with a socket. Prior liners that have added thickness do not have thicker areas specifically located to provide bone control through added compression at target areas and attachment areas dimensioned to provide for relief areas between attachment areas and, thus, do not stabilize the skeletal structures of the limb within the socket.

The SSLS can be worn over the limb and inside the traditional or compression stabilized socket. In the case of a traditional socket, the SSLS modifies the peripheral volume compression so that enhanced compression is applied to target areas. In the case of a compression stabilized socket, the SSLS augments the compression to target areas to account for lost limb volume. The clinician or wearer can also address other concerns regarding inadequate compression identified after the compression stabilized socket is fabricated. In one embodiment, four generally longitudinally oriented, externally affixed pockets or receptacles are located at and overlay attachment areas on the external surface of the liner in areas associated with target areas of the residual limb. In another embodiment, four generally longitudinally oriented attachment areas, such as hook and loop strips, or Velcro® strips, are located at and overlay attachment areas on the external surface of the liner. In another embodiment, three attachment areas may be sufficient to provide the desired bone control.

In one embodiment, at least one attachment area is oriented along the longitudinal dimension of the liner in a discontinuous configuration such that it comprises two or more sub-areas lined up along the length of the attachment area to function as a single attachment area. In another embodiment, two or more shims are similarly aligned over a uniform or discontinuous attachment area to function as a single shim. In yet another embodiment, a very short attachment area is coupled with a shim of sufficiently longer length so as to provide the desired bone control based on the length of the shim, rather than the length of the attachment area.

In a variation of either of the four attachment area embodiments, the centerlines of the attachment areas are placed circumferentially and approximately equally spaced apart at 90 degree increments from one another. In one application of this embodiment, the clinician or user aligns the longitudinal midline of the anterior surface of the residual limb to an alignment indicator or a reference on the liner that is equal to 0 degrees, and the SSLS is donned by the wearer so that the centerlines of the attachment areas are at 45, 135, 225, and 315 degrees relative to that alignment indicator or reference once the SSLS is on the residual limb. It is to be appreciated that the particular anatomy of a wearer or expectations of asymmetrical limb loads on a particular limb will dictate the location of the wearer's target areas. Therefore, the clinician may require the liner be fabricated with attachment areas in different locations.

In one embodiment, the attachment area has a narrowest width of at least approximately 4.7% of the limb circumference, but a narrower width may be selected in particular applications. The attachment area has a broadest width adapted to permit a plurality of relief areas between each attachment area for displacement of tissue of the residual limb.

In one embodiment with hook and loop strips overlaying attachment areas, each attachment area is configured so that it can receive or couple with a shim selected by a clinician or wearer from an inventory of shims of varying length, width, thickness, curvature, and shape. Once donned, each shim adds an additional thickness to the attachment areas of the liner in order to increase the compression normally provided by the socket and SSLS (without shims) to a level that minimizes motion of the underlying bone. In one embodiment, shims are manufactured with portions that snap-off to allow the clinician to easily modify the shim shape (length or width) to match a wearer's unique target area, even in the case where a pre-selected SSLS has an attachment area that may be longer or shorter than that wearer's corresponding target area. In still another embodiment, the shims can be thermo-formed to add desired curvature.

One shim embodiment is made of plastic, but other suitable material may be used. A thermo-formed shim embodiment is made of carbon composite, but other suitable material may be used. Yet another embodiment of the shim is made of a sealed gel packet, where the gel is made of silicone material, but urethane or other suitable material may also be used. It is to be appreciated that such gel material could also be enclosed directly into a pocket of a SSLS embodiment and the pocket sealed, so that that the attachment area is comprised of such gel material. In SSLS embodiments where the shim or gel is of sufficiently low durometer, the SSLS can be donned or doffed while the shim, gel, or gel packet remains in the pocket or otherwise attached to the liner.

In another liner embodiment, gel is embedded directly into the liner materials at the attachment areas to provide the increased radial thickness desired for bone control.

In other embodiments, the gel or a low durometer shim is permanently adhered to the inner surface of the liner at attachment areas during fabrication, such as by placing the gel or a low durometer shim on a positive model of the limb and fabricating the liner over the top of the gel or shim and the positive model. In another embodiment, attachment areas on the inner side of the liner (the side facing the limb) allow the wearer to roll-on the liner over gel packets pre-placed on the limb at target areas to achieve the desired compression and bone control. In a variation of this embodiment, shims of appropriate durometer are pre-placed on the limb instead of gel packets. In embodiments where the inner side attachment areas are pockets, the wearer can insert shims or gel packets into the pockets prior to or after donning the socket without requiring pre-placement on limb target areas. Where the gel packets or shims have an appropriately low durometer, these inner pocket embodiments can be roll-on liners even with the shims or gel packets inserted before donning.

Whether embedded or contained in sealed gel packets, in some embodiments the gel properties are variable or controllable when subjected to temperature changes, shear forces, electrical charge, or magnetic fields to cause the gel durometer or volume to change. Increasing the volume of the gel is advantageous to increase the radial thickness at the attachment areas when the limb is subjected to shear loads, increased temperature after donning, or when desired by the user or clinician (in the case of electrically or magnetically controllable gels). Increasing the durometer of the gel is advantageous for bone control because it causes the liner to resist compressive forces on the liner between the limb and socket and maintain radial thickness that might otherwise be reduced due to the compressive force. Conversely, an embodiment with a gel whose durometer decreases in response to high shear forces is advantageous for donning a roll-on liner.

Gels with these properties are known in the art and include shear-thinning, shear-thickening, magneto rheological, electrorheological, and thermoresponsive gels.

The SSLS is suitable for use with pre-existing sockets. However, where an SSLS will be used with a socket that has not yet been fabricated, an embodiment of the SSLS can be used during the casting process with or without the shims in order to set the appropriate internal volume of the prosthetic socket when the socket is fabricated. Similarly, the appropriate internal volume of the prosthetic socket can be set using an embodiment of the SSLS during a scanning process, such as when laser scanning the residual limb to create a virtual solid model of the limb, again with or without the shims. Use of a SSLS embodiment during casting or scanning is advantageous because the socket volume may otherwise be too small and the socket may not properly don if no SSLS was used during the casting or imaging process. In other words, after the wearer donned the SSLS on the residual limb, the wearer may have difficulty sliding the fabricated socket over the residual limb and SSLS.

Embodiments of the SSLS may be a traditional closed-ended design, but other embodiments can be in an open-end sleeve configuration. One embodiment of the SSLS is constructed of elastomeric material, but silicone or other suitable materials can be used. In embodiments with a pocket, the pocket material that is attached to the liner to form the pocket can be made of elastomeric material, fabric, silicone, or other suitable material. In one pocket embodiment, the pocket opening for inserting the shim is located on the proximal end of the pocket, but the pocket opening can be in any location such that the shim can be inserted and removed from the pocket.

In one embodiment, pocket material surrounds and adheres to the liner to form a second liner layer and additional pocket material attaches to the second liner layer to form one or more pockets for one or more shims.

In an embodiment where an attachment area is made of hook or loop fasteners, an embodiment of the shim also has at least one shim face covered with corresponding hook or loop material, so that it may be attached to the attachment area.

In other embodiments, the socket-facing surface of the shims or pockets includes a raised texture such that friction is increased against the socket wall to resist or prevent slippage of the liner with respect to the socket wall. This raised texture could be uni-directional such that it prevents rotation or pistoning, or bi-directional, or multidirectional such that shear in any direction is mitigated or reduced.

In some embodiments with pocket or hook and loop attachments, the thickness of the pocket and hook and loop attachment material or the underlying liner material is increased in the attachment area so that the pocket or the attachment material or underlying liner material provides some of the desired compression to the wearer even when no shim is inserted or attached. In one embodiment, the thickness of the liner is increased in the attachment area by bonding an additional liner material layer on top of the primary liner material that constitutes the primary liner surrounding the residual limb after donning. The additional liner material layer can be of variable thickness to provide for tapering at the edges of this additional material.

In another embodiment where the thickness of the liner is increased in the attachment area without use of a shim, the liner itself is molded or otherwise fabricated to be thicker in the attachment areas, rather than by bonding an additional liner material layer on top of the primary liner material. In a variation of either this embodiment or the embodiment with the additional liner material bonding, there is no mechanism for attaching shims because the thickness manufactured into the liner is sufficient to provide the desired bone control.

In other embodiments, bladders are affixed externally or fabricated within the liner in the attachment areas such that the radial thickness at the attachment areas can be increased as bladder volume is increased using a hand pump coupled to each bladder. The hand pump is detachable in these embodiments, but in other embodiments, the hand pump could attach to a suitable location on the liner or socket, once the socket is donned. It is to be appreciated that a $CO_2$ cartridge and regulator or an automated pump could be substituted for the hand pump, and that fluids other than air or $CO_2$ could be used as the inflation medium.

Besides the advantages already identified, the SSLS has a number of other advantages over other known liners. For instance, because embodiments of the SSLS liners can be produced in a variety of customizable and formable shapes and configurations, these embodiments can be sold as a product or kit with shims, so that the SSLS is readily usable by clinicians and wearers to assemble a customized liner. This ability to mass produce the SSLS means the product can be produced at a significantly reduced cost as compared to current customized solutions.

Another advantage of the SSLS is that, in some embodiments, a clinician or wearer can alter the fit on the fly by simply adding or subtracting shims, including doubling or tripling the number of shims at an attachment area or, in still another embodiment, utilizing shims of different lengths, widths, thicknesses, curvatures, and shapes.

In a disposable embodiment, all or portions of the SSLS can be manufactured with materials whose cost and fabrication make it economical to dispose of these portions on a daily or monthly basis.

In other embodiments, one or more sensors can be integrated into or attached to one or more shims and be in wireless communication with a smartphone or other computer device to provide socket and SSLS fit information, such as localized pressure, during all phases of the wearer's use of the socket. Similarly, in other embodiments, one or more sensors could be attached to or integrated into one or more attachment areas of the SSLS.

DETAILED DESCRIPTION OF THE INVENTION

Figure 1:
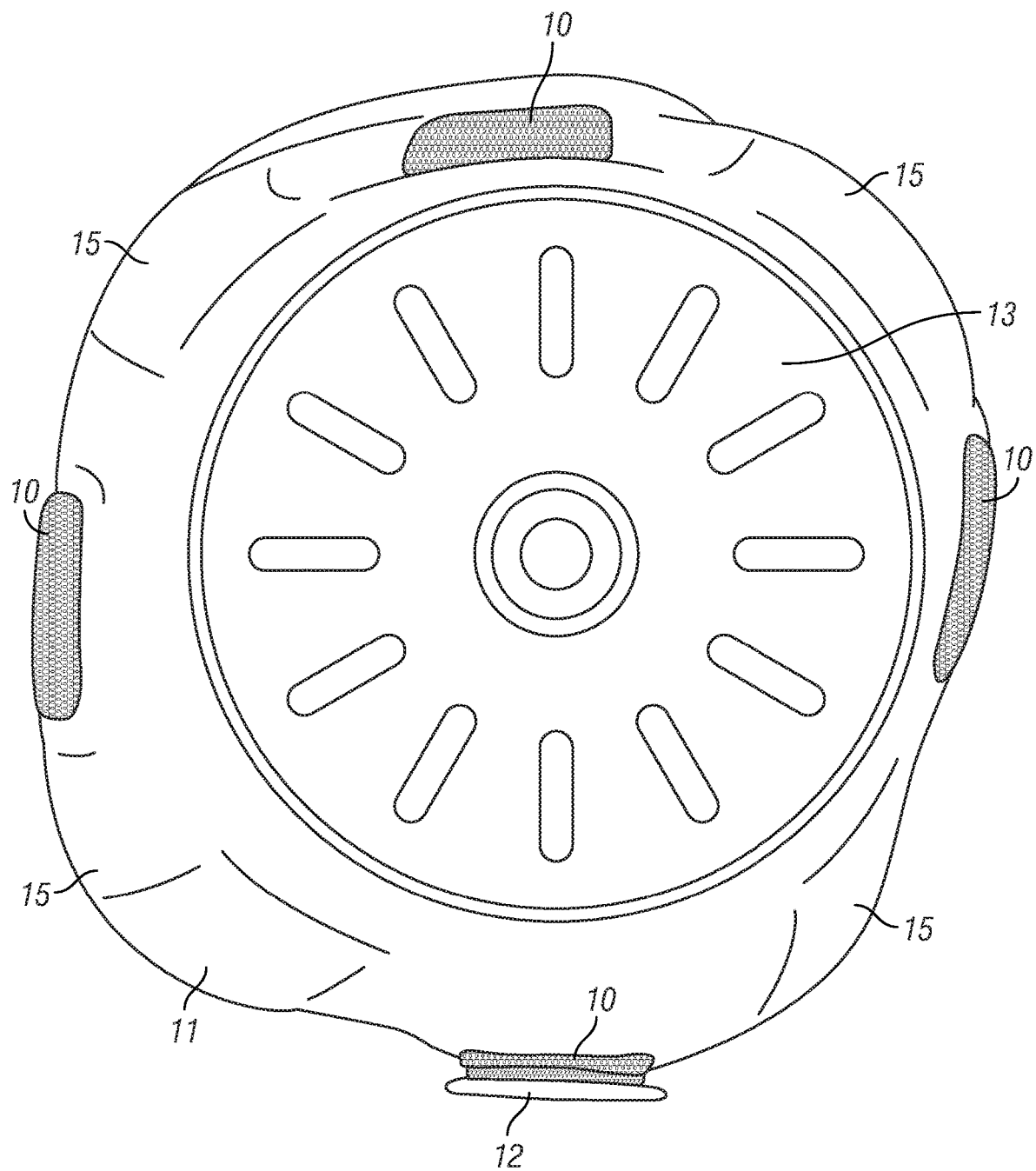
FIG. 1 depicts an SSLS embodiment looking up from its bottom end, at the distal end of the SSLS.

FIG. 1 depicts an SSLS embodiment looking up from its bottom end 13, at the distal end of the SSLS. The liner 11 in this embodiment includes four longitudinally oriented attachment areas 10 made of hook and loop strips that are affixed to the external surface of the liner in areas associated with target areas of the residual limb.

Figure 2:
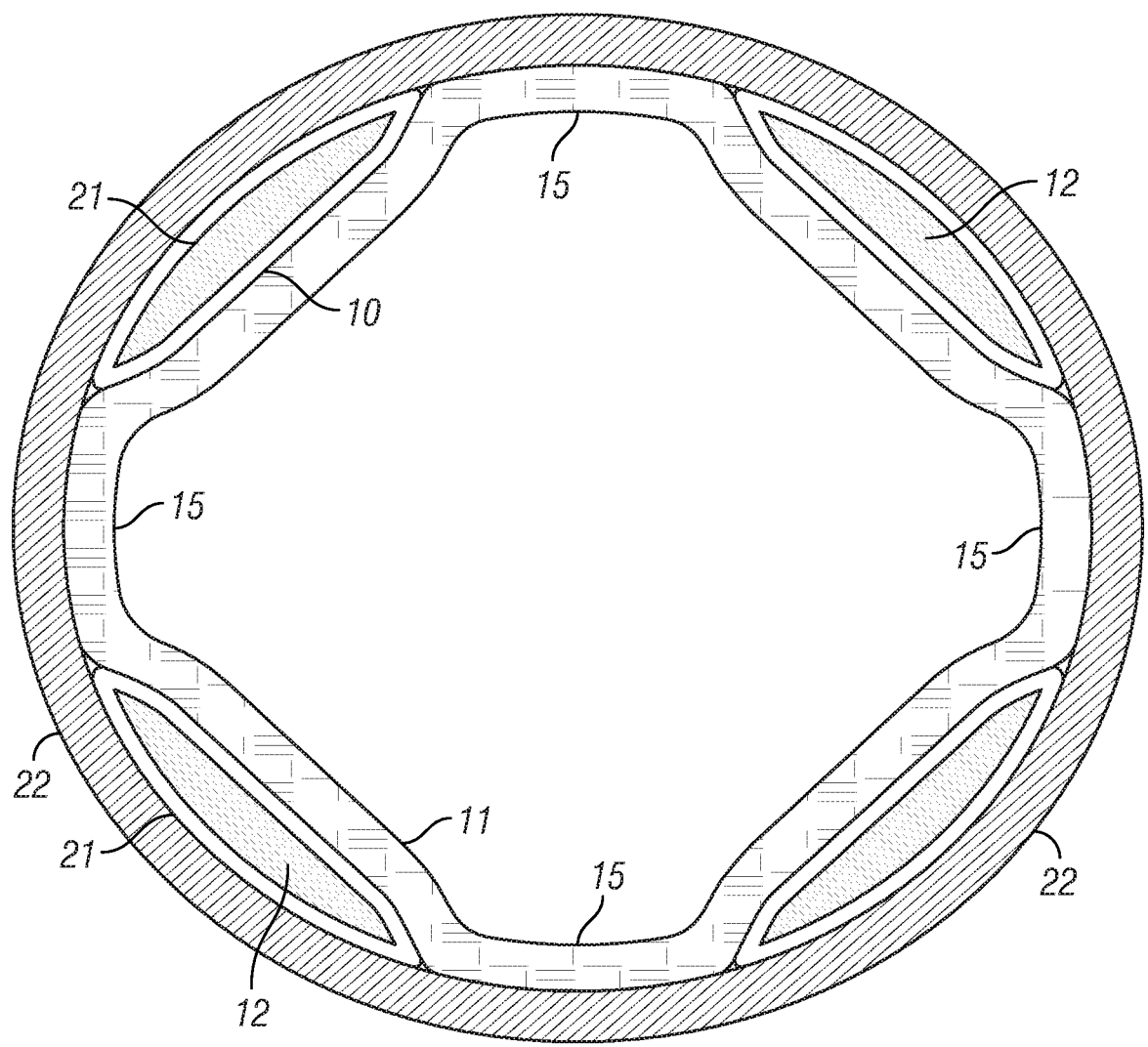
FIG. 2 depicts a cross-sectional view of another embodiment of the SSLS, where the liner has affixed to its external surface four longitudinally oriented, external pockets.

FIG. 2 is a cross-sectional view of another embodiment of the SSLS, where the liner 11 has affixed to its external surface four longitudinally oriented, external pockets 21, also in areas associated with target areas of the residual limb. The SSLS in FIG. 2 is also shown inserted in a socket 22.

In the embodiments shown in FIG. 1 and FIG. 2, the centerlines of the attachment areas 10 are placed circumferentially and approximately equally spaced apart at 90 degree increments from one another. In one application of this embodiment shown in FIG. 4, the clinician or user aligns the longitudinal midline of the anterior surface of the residual limb with a reference line 43 that represents 0 degrees, and the SSLS is donned by the wearer so that the centerlines of the attachment areas are at approximately 45, 135, 225, and 315 degrees relative to the reference line once the SSLS is on the residual limb and the reference line is aligned with the midline of the anterior surface of the residual limb. It is to be appreciated that the liner can have alignment indicators other than a reference line that are also suitable for assisting the clinician or user in aligning the liner attachment areas so that the attachment areas are at approximately 45, 135, 225, and 315 degrees relative to the longitudinal midline of the anterior surface of the residual limb.

In FIG. 1, the attachment areas have a narrowest width of approximately 5.9% of the limb circumference, but a narrowest width of at least approximately 4.7% of the limb circumference may be selected, or narrower widths may be selected in particular applications. In FIG. 1, the attachment areas have a broadest width of approximately 8.5% of the liner circumference, but the attachment areas may have a broadest width adapted to permit a plurality of relief areas 15 between each attachment area for displacement of tissue of the residual limb. The plurality of relief areas 15 are also shown in FIG. 2.

Figure 3:
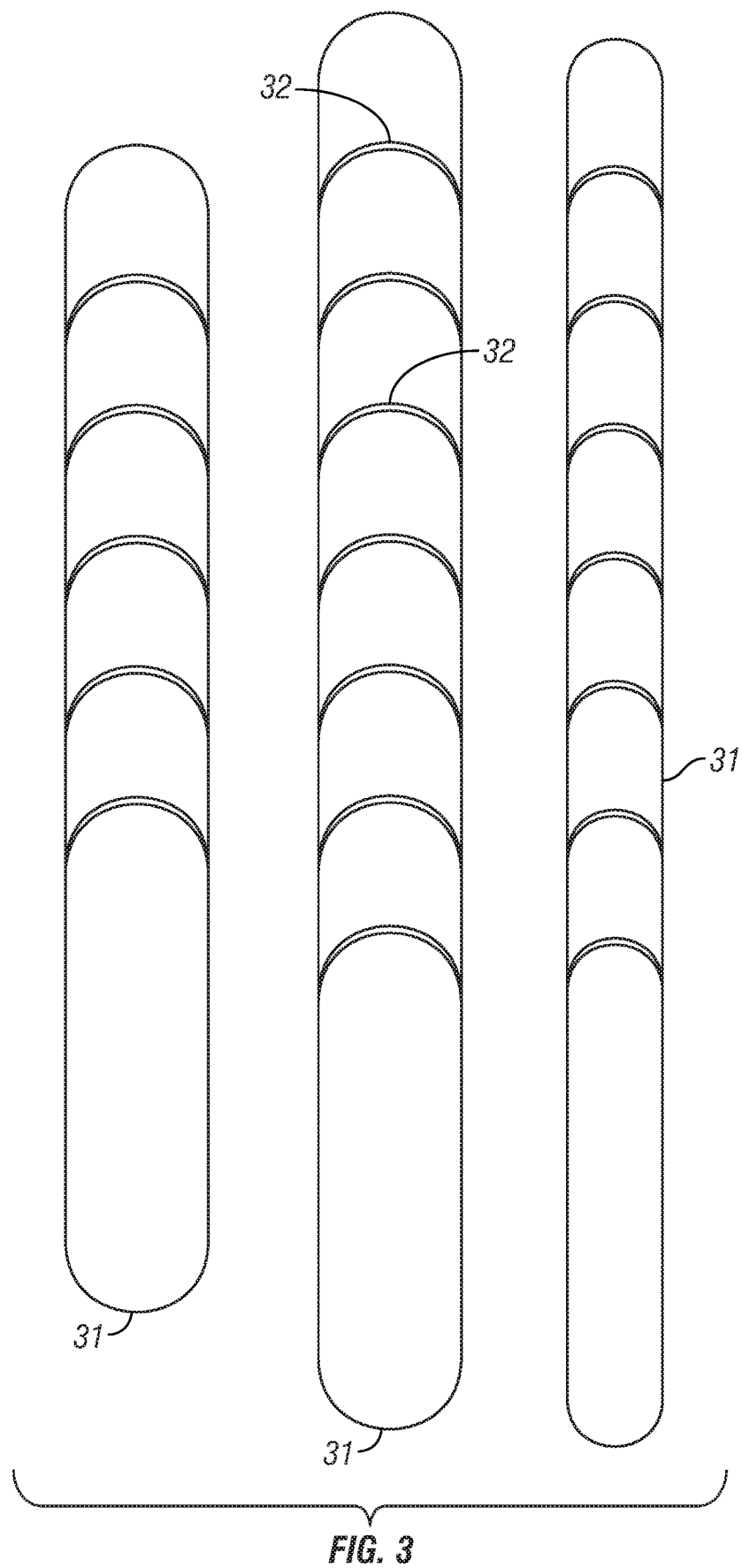
FIG. 3 depicts an inventory or kit of shims for an embodiment of the SSLS from which the clinician or wearer may select a shim or shims.

Each attachment area is configured so that it can receive or couple with a shim 12, as shown in FIG. 1 and FIG. 2. FIG. 3 depicts an inventory or kit of shims 31 from which the clinician or wearer may select a shim. The shims in this inventory or kit vary in length, width, and thickness, but the inventory may also include shims of different curvatures, or shape. The shim embodiments depicted in FIG. 3 are 1.6 and 2.4 mm thick (thickness not shown), but shims of approximately 0.8 mm or larger would be suitable, depending on the fit of the socket.

Once attached to an attachment area, each shim adds an additional thickness to the attachment area of the liner in order to increase the compression normally provided by the socket and SSLS (without shims) to a level that minimizes motion of the underlying bone. In the embodiment shown in FIG. 3, the shims are manufactured so that portions easily snap-off at the curved lines 32 to allow the clinician to modify a shim length to match a wearer's target area. In other embodiments (not shown), different snap-off features allow the clinician to easily modify the shim width, again to match the wearer's target area. In still other embodiment (not shown), the shims can be thermo-formed to add desired curvature The shim embodiments shown in FIG. 3 are made of plastic, but other suitable material may be used. A thermo-formed shim embodiment (not shown) is made of carbon composite, but other suitable material may be used. Yet another embodiment of the shim is made of a sealed gel packet (not shown), where the gel is made of a silicone material, but urethane or other suitable material may be used. It is to be appreciated that such gel material could also be enclosed directly into a pocket of a SSLS embodiment and the pocket sealed, so that that the attachment area is comprised of such gel material. In SSLS embodiments where the shim or gel is of sufficiently low durometer, the SSLS can be donned or doffed while the shim, gel, or gel packet remains in the pocket or otherwise attached to the liner.

Figure 11:
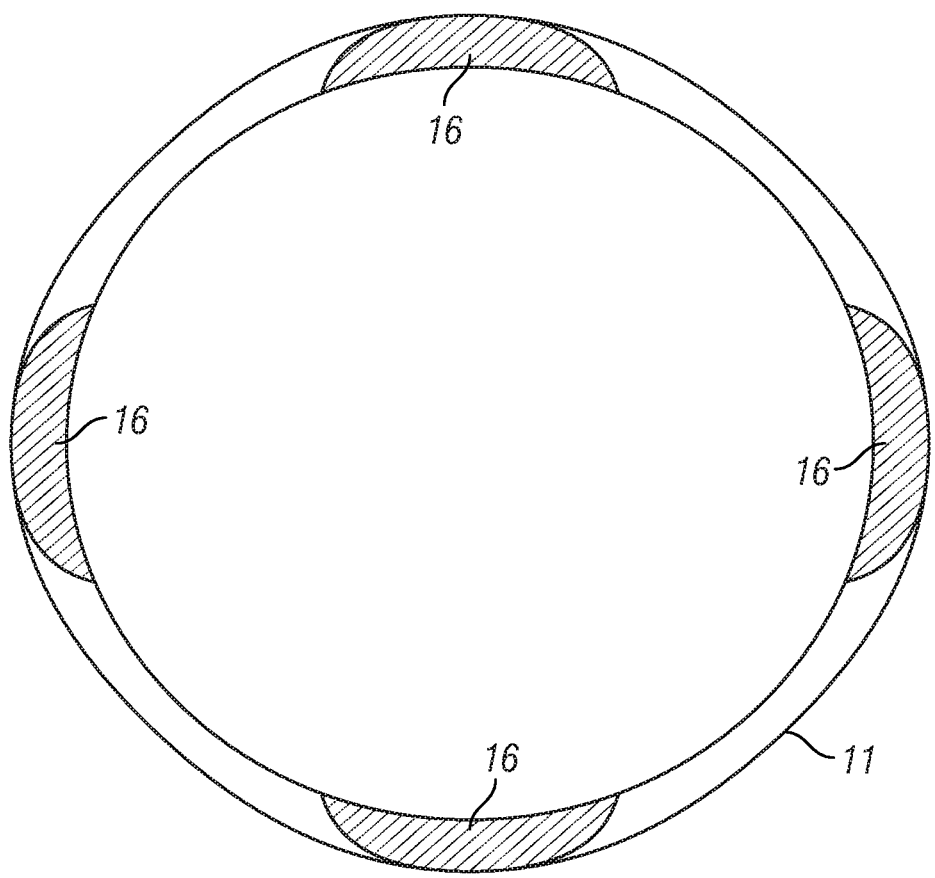
FIG. 11 depicts a cross-sectional view of an embodiment where gel is embedded directly into the liner at the attachment areas to provide the increased radial thickness desired for bone control.

FIG. 11 depicts another liner embodiment where gel 16 is embedded directly into the liner 11 at the attachment areas to provide the increased radial thickness desired for bone control.

Where an SSLS will be used with a socket that has not yet been fabricated, an embodiment of the SSLS can be used during the casting process with or without the shims in order to set the appropriate internal volume of the prosthetic socket when the socket is fabricated. Similarly, the appropriate internal volume of the prosthetic socket can be set using an embodiment of the SSLS during a scanning process, again with or without the shims.

Figure 4:
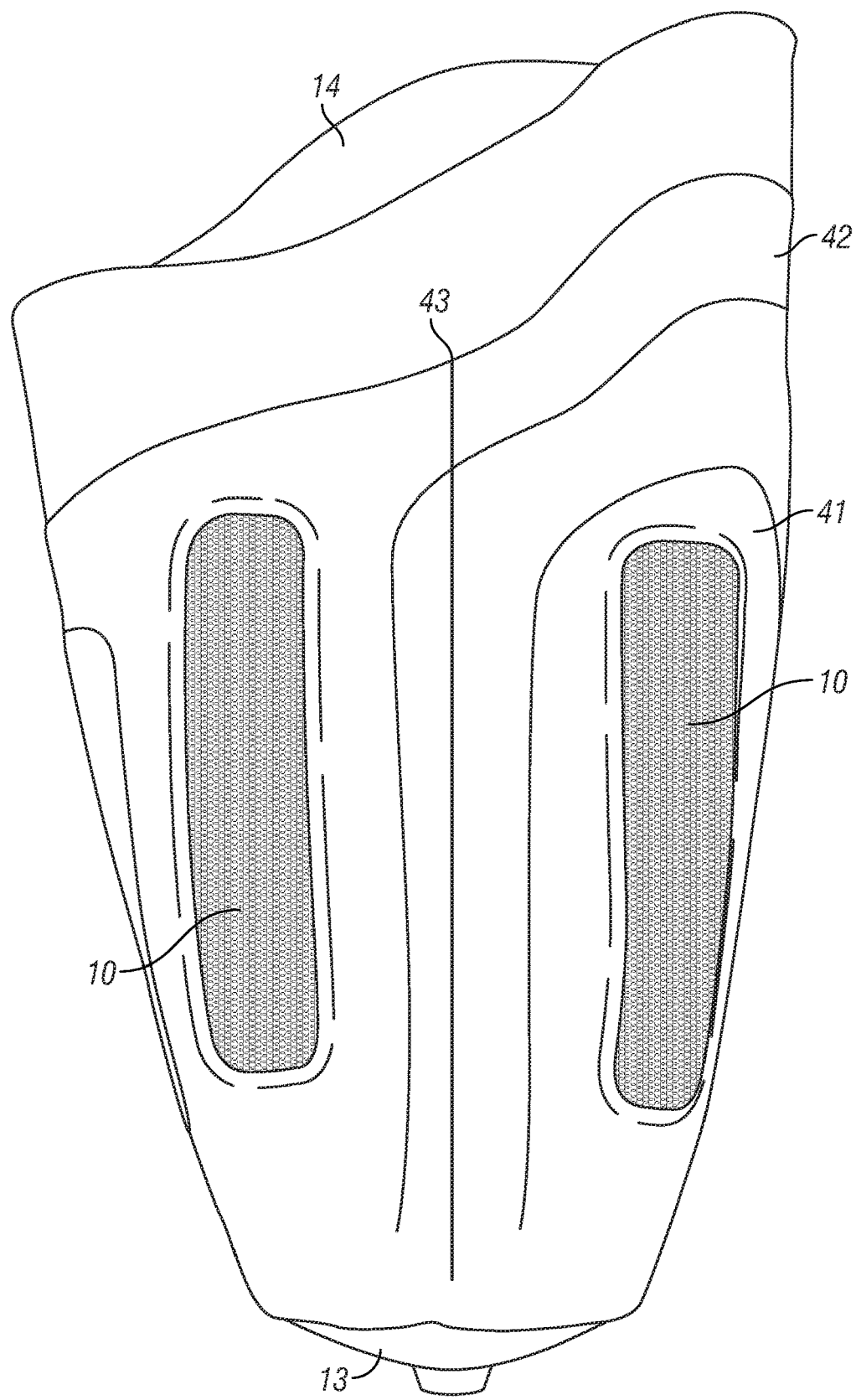
FIG. 4 depicts an embodiment of the SSLS in a traditional closed-ended design.
Figure 5:
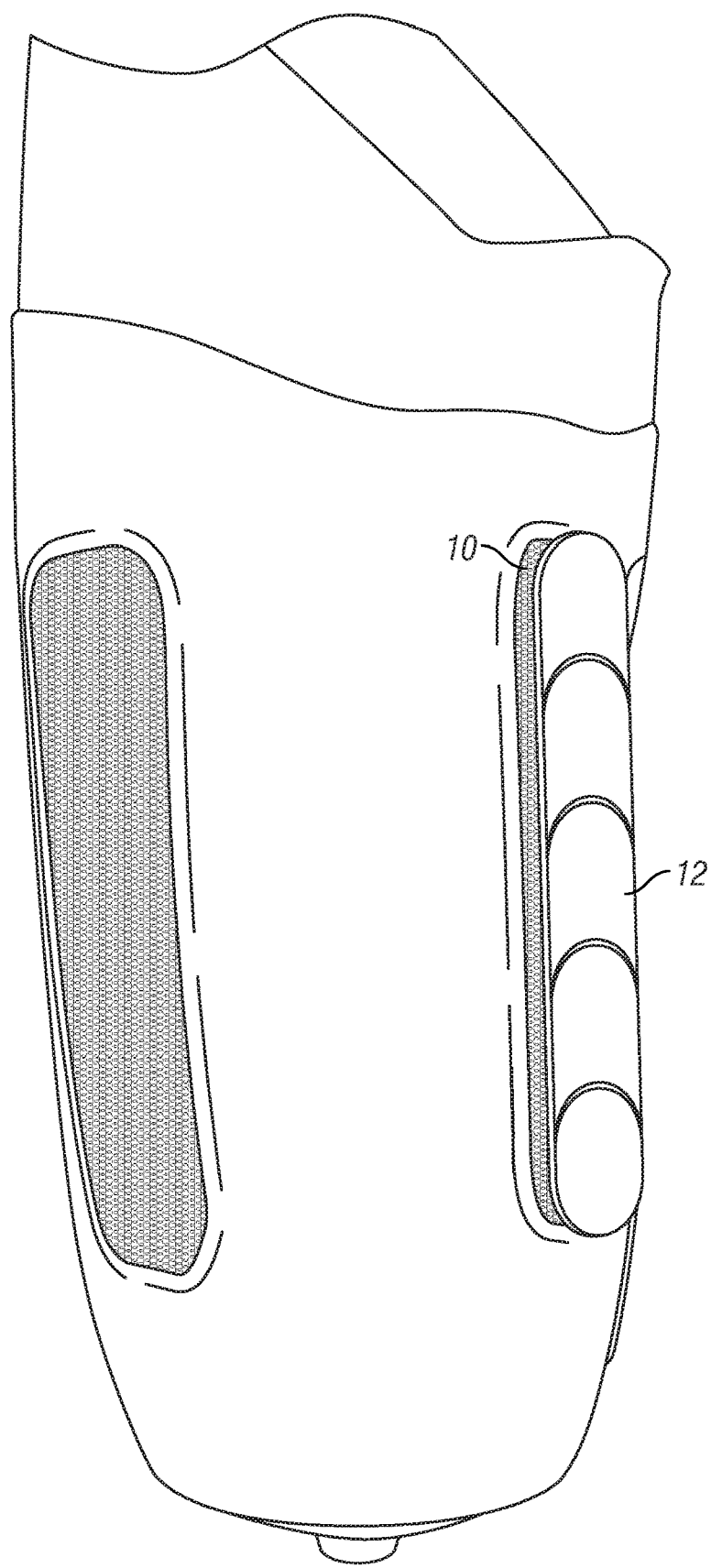
FIG. 5 depicts an SSLS embodiment with a shim attached to one of the attachment areas.
Figure 6:
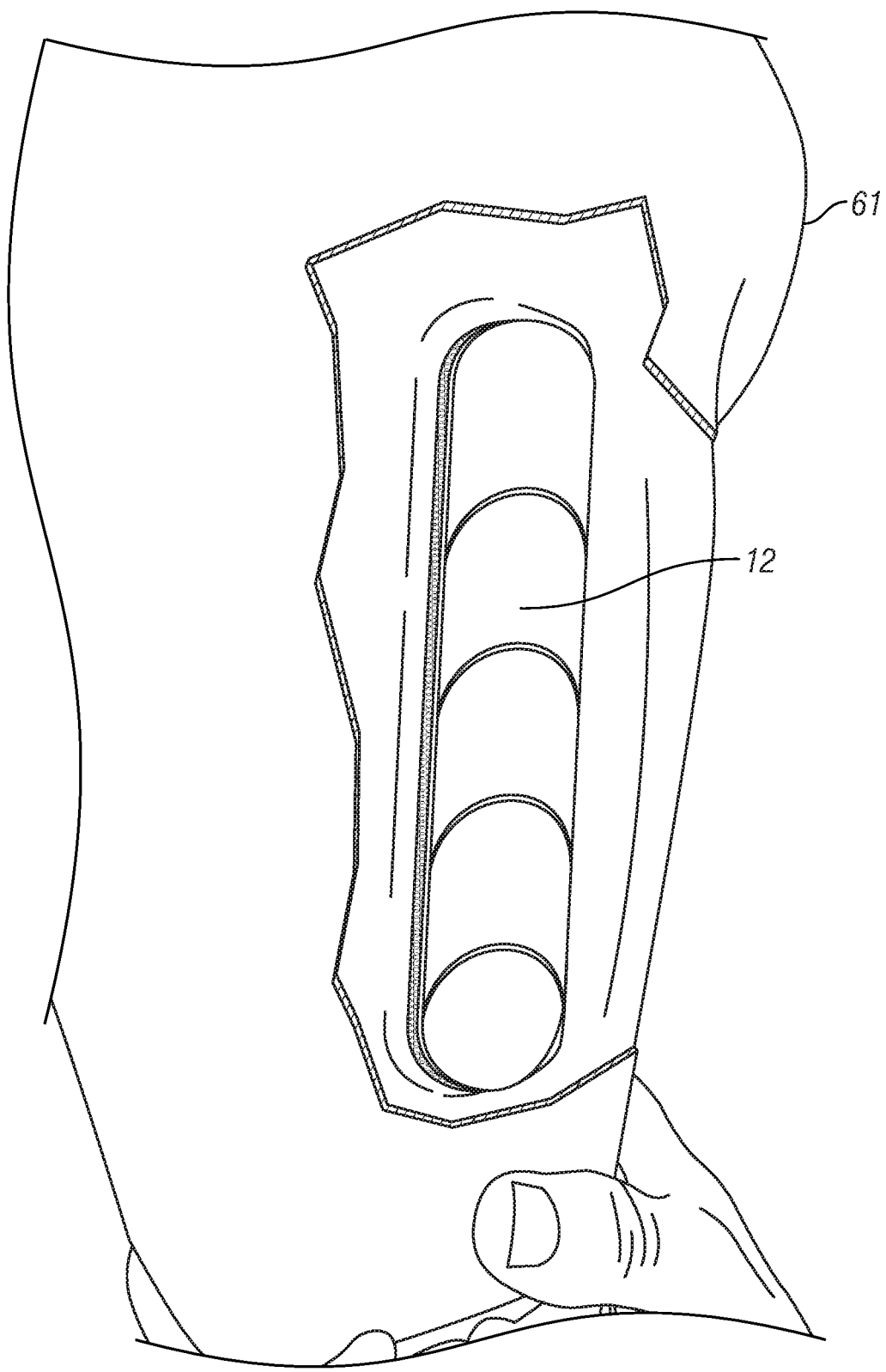
FIG. 6 depicts the SSLS embodiment inserted into a compression stabilized socket, which is cut-away to show the SSLS, including a shim mounted to the attachment area.

FIG. 4 depicts an embodiment of the SSLS in a traditional closed-ended design, but other embodiments can be in an open-end sleeve configuration. FIG. 5 depicts an SSLS embodiment similar to that in FIG. 4, but showing a shim 12 attached to one of the attachment areas 10. FIG. 6 depicts the SSLS inserted into a compression stabilized socket 61, which is cut-away to show the SSLS, including a shim 12 mounted to the attachment area.

The embodiment of the SSLS depicted in FIG. 4 has a rigid bottom 13, but non-rigid materials may also be used, or the bottom may be a continuation, for example, of the liner 42 material and attached at the distal end to form a sock-like configuration. The embodiment in FIG. 4 is constructed of elastomeric material, but other suitable materials could be used.

Figure 7:
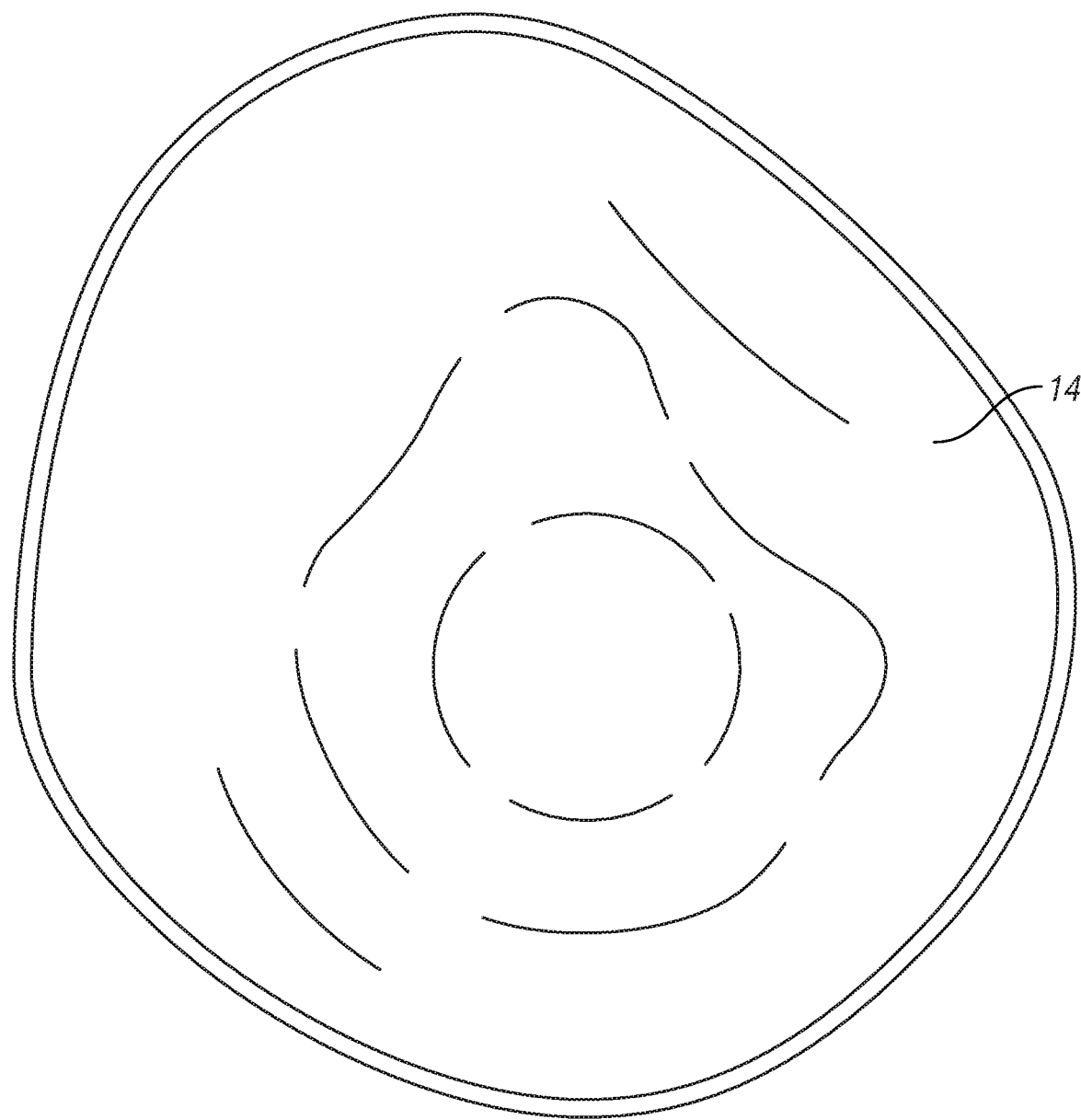
FIG. 7 depicts a top view of an SSLS embodiment showing the open top.

In the SSLS embodiment depicted in FIG. 4, the liner is open at the top 14 or proximal end to receive the residual limb. FIG. 7 depicts a top view of this embodiment showing the open top 14.

Figure 8:
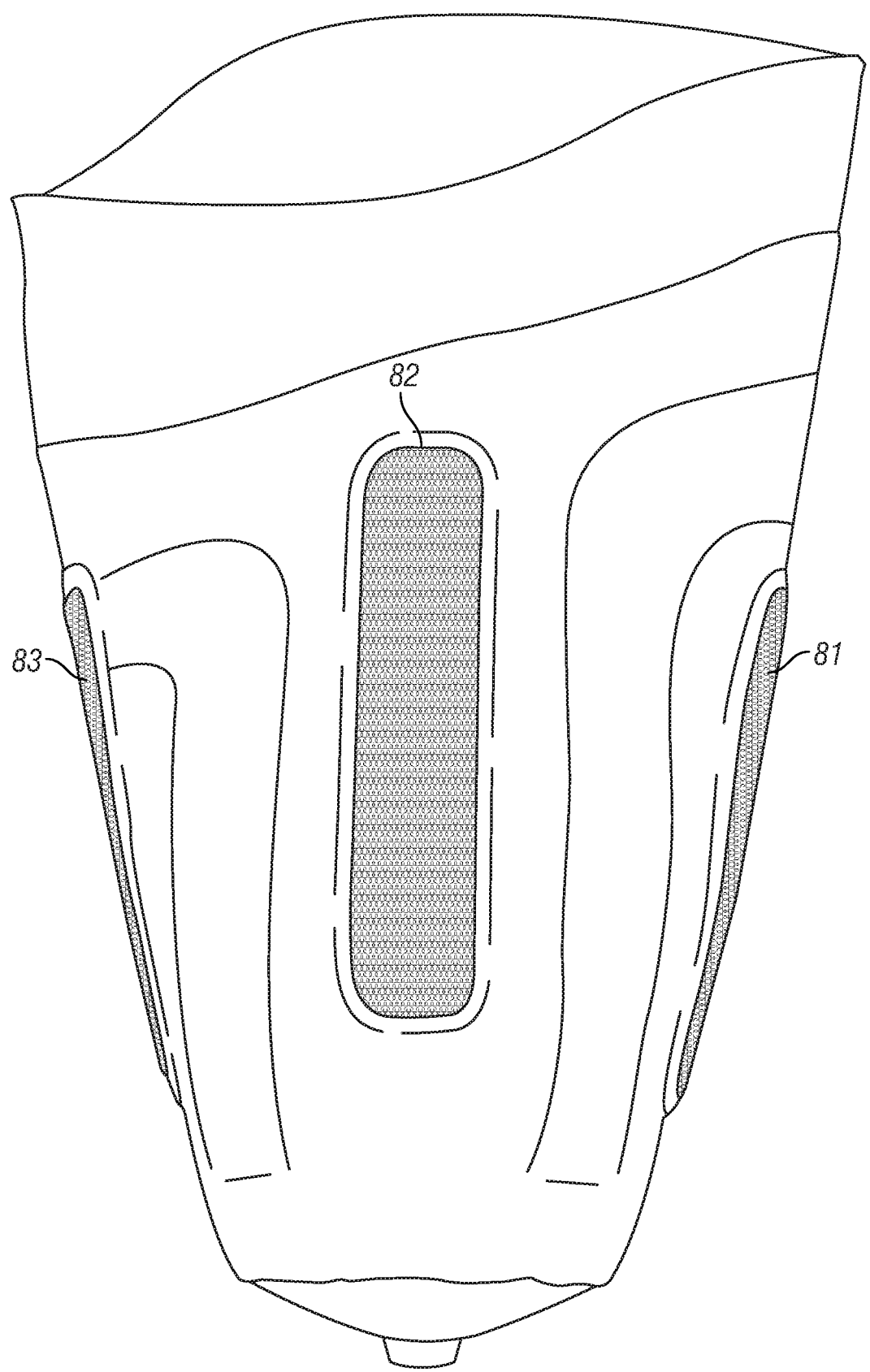
FIG. 8 depicts an embodiment of the SSLS showing generally longitudinally oriented attachment areas whose vertical placement varies to align with respective target areas of a wearer once the SSLS is donned.

FIG. 8 depicts an embodiment of the SSLS with a first attachment area 81, a second attachment area 82, and third attachment area 83, each approximately 90 degrees apart. These attachment areas are generally longitudinally oriented, but their vertical placement varies so that they are aligned with respective target areas of a wearer once the SSLS is donned. For instance, the first attachment area 81 is shorter and extends more distally than the second attachment area 82.

In the embodiment depicted in FIG. 8, the shortest length of the attachment area is approximately 35% of the liner length, however, a shorter attachment area, such as 10% of the liner length, or even shorter, can be selected in particular applications, where the liner length means the finished length of the liner as worn by a wearer and as generally depicted in the drawings of this application. It is to be appreciated that liner embodiments using very short attachment areas coupled with shims with longer lengths, such as shim lengths that are 10% or more of the liner length, would be within the spirit and scope of the invention since in such embodiments it is the overall length of the shim that primarily defines the length of the compression area.

In the pocket embodiment depicted in FIG. 2, the pocket 21 material that is affixed to the liner 11 may be made of elastomeric material, fabric, silicone, or other suitable material. In this embodiment, the pocket opening for inserting the shim 12 is located on the proximal end of the pocket, but the pocket opening can be in any location such that the shim can be inserted and removed from the pocket.

In a variation of the embodiment depicted in FIG. 2, the pocket 21 material surrounds and adheres to the liner 11 to form a second liner layer (not shown) and additional pocket material attaches to the second liner layer to form one or more pockets for one or more shims 12.

Figure 9:
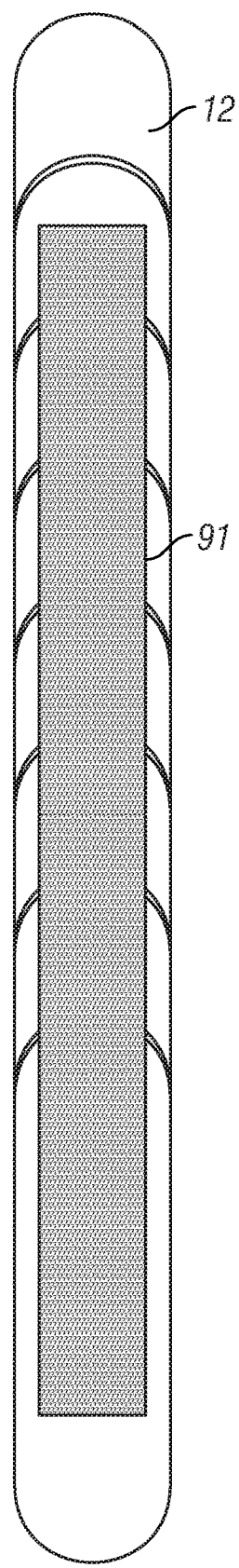
FIG. 9 depicts an embodiment of a shim where a face of the shim is covered with hook or loop fastener material to correspond with the hook or loop fastener material used for an attachment area.

FIG. 9 depicts an embodiment of the shim 12 where a face of the shim is covered with hook or loop fastener material 91 to correspond with the hook or loop fastener material used for an attachment area 10 (shown, for example, on FIG. 1 and FIG. 4), so that the shim may be attached to an attachment area.

In the embodiments depicted in FIG. 1 and FIG. 2, the thickness of the hook and loop attachment area 10 material and the pocket 21 material increases the attachment area thickness so that the pocket or the attachment material provides some of the desired compression to the wearer even when no shim is inserted or attached. For example, in the embodiment shown in FIG. 1, the loop strip is approximately 0.4 mm thick. In another embodiment (not shown), the underlying liner 11 material may be fabricated or modified to be thicker in the attachment area to provide the desired compression to the wearer even when no shim is inserted or attached.

In the embodiment shown in FIG. 4, the thickness of the SSLS liner is increased in the attachment area by bonding an additional liner material layer 41 on top of the primary liner 42 material that surrounds the residual limb after donning. The additional liner material layer can be of variable thickness to provide for tapering at the edges of this additional liner material.

In other embodiments (not shown), one or more sensors can be integrated into or attached to one or more shims 12 and be in wireless communication with a smartphone or other computer device to provide socket 22 and SSLS fit information, such as localized pressure, during all phases of the wearer's use of the socket. Similarly, in other embodiments (not shown), one or more sensors can be attached to or integrated into one or more attachment areas 10 of the SSLS.

Figure 10:
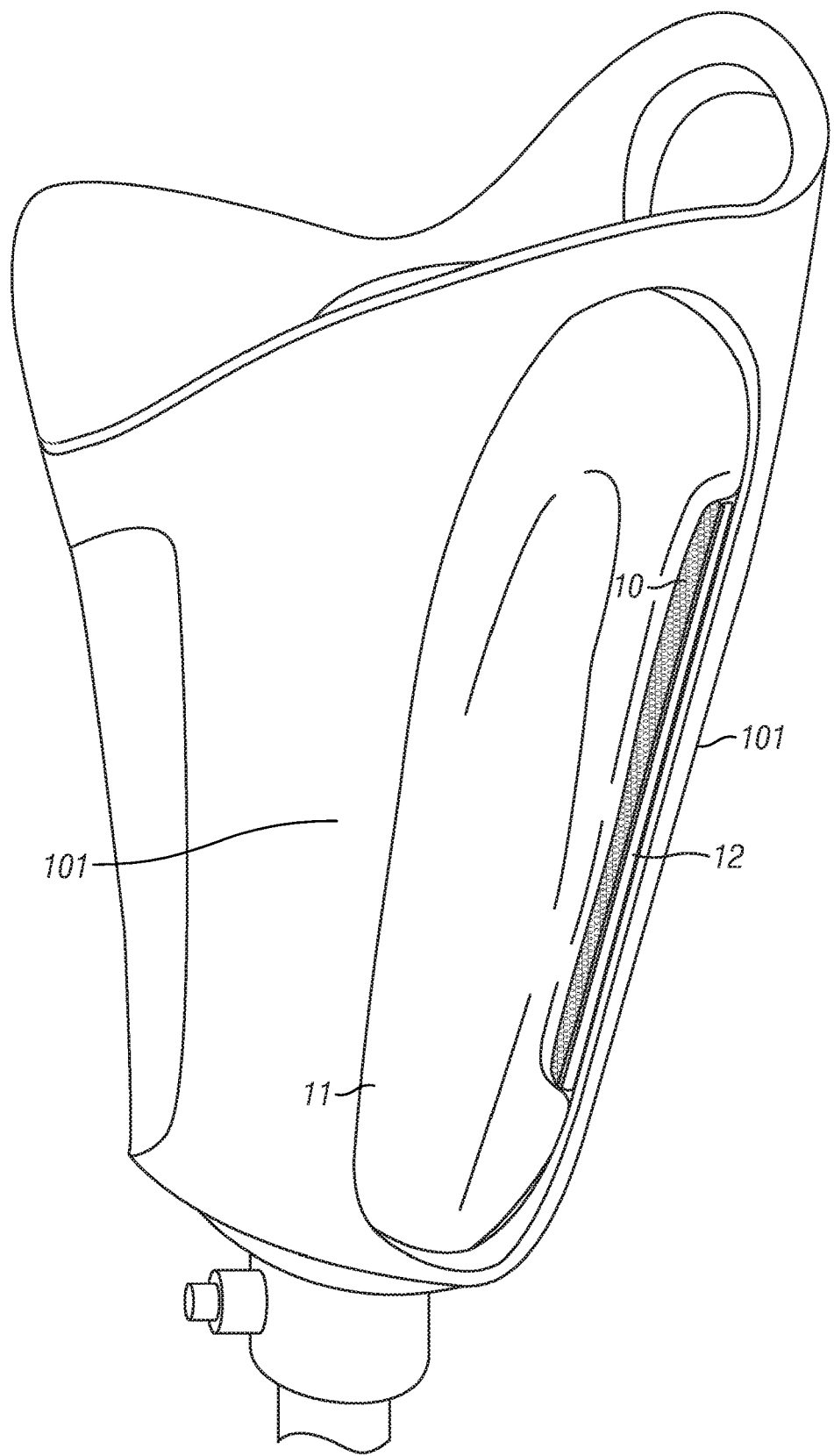
FIG. 10 depicts an SSLS embodiment inserted inside an open-cage compression stabilized socket so that the attachment area affixed to the liner is aligned with one of the compression struts and a shim is attached to the attachment area.

FIG. 10 depicts the SSLS inserted inside an open-cage compression stabilized socket. In this embodiment, the attachment area 10 is aligned with one of the compression struts 101, so that a shim 12 can be attached to the attachment area affixed to the liner 11, resulting in increased compression on the residual limb as compared to if no shim were attached.

Liner Fabrication and Shim Use

An exemplary method for fabricating the liner for the SSLS comprises selecting at least three attachment areas on a liner lying along a longitudinal dimension of the liner, wherein the longitudinal dimension runs from the distal end to the proximal end of the liner, wherein each attachment area has a centerline, wherein the selecting at least three attachment areas further comprises: substantially aligning each centerline parallel to the longitudinal dimension; spacing each attachment area centerline circumferentially and approximately equally around the liner; selecting a circumferential width of each attachment area in such a way as to permit a plurality of relief areas between each attachment area, wherein the liner has a minimum radial thickness; selecting a length of each attachment area, wherein each attachment area is adapted to extend at least approximately 10% the longitudinal dimension; a) selecting a first attachment area material; b) dimensioning the first attachment area material to overlay a first attachment area; and c) affixing the first attachment material to the liner in such a way as to overlay the first attachment area to form a first enhanced compression area; repeating steps a)-c) with additional attachment area materials and the remainder of the attachment areas to form a plurality of enhanced compression areas, wherein the plurality of enhanced compression areas includes the first enhanced compression area, wherein a maximum radial thickness of each of the plurality of enhanced compression areas is at least 0.4 mm greater than the minimum radial thickness.

It is to be appreciated that the step of spacing each attachment area centerline circumferentially and approximately equally around the liner may be adjusted by a fabricator to accommodate the particular anatomy of a wearer or asymmetrical limb loads expected during use, such as higher anterior and lateral loads that a particular fabricator may anticipate for humeral applications.

In a variation of this method, the first attachment area material and the additional attachment area materials comprise sealed pocket material, further comprises selecting a thickness of the first attachment area material and the additional attachment area materials in such a way as to prevent substantial movement of a skeletal structure within the limb when the liner is worn with a socket.

Besides using the exemplary method for fabricating the liner, the liner can also be integrally formed by a variety of molding processes, including casting, injection molding, extrusion molding, thermoforming, and rotational molding, It is to be appreciated that one skilled in the art can embed additional liquid or solid materials or gels into the liner at attachment areas in accordance with the invention using methods known in the art to cause the thickness of the attachment areas to be sufficiently greater relative to the thickness of the liner outside the attachment areas, so that the liner provides the desired bone control.

Additional steps for adding shims to the liner of the SSLS comprise: a) selecting an enhanced compression area from the plurality of enhanced compression areas; b) selecting a shim to attach to the enhanced compression area, wherein the shim is selected from an inventory of shims of at least one varying dimension selected from the group consisting of length, width, radial thickness, and curvature; c) attaching the shim to the enhanced compression area, d) repeating steps a)-c) with additional shims and the remainder of the plurality of enhanced compression areas as necessary to prevent substantial movement of the skeletal structure within the limb when the liner is worn with a socket.

In a variation of this method for adding shims, the step of attaching a shim to the enhanced compression area comprises attaching two or more shims to the enhanced compression area.

A variation of the exemplary method for fabricating the liner comprises selecting the liner from a kit of component parts comprising a variety of liner shapes and configurations.

In a variation of the method for adding shims to the liner, the shim and the additional shims have a maximum durometer adapted to permit a user to don and doff the liner while the shims are attached to the liner.

A variation of the exemplary method for fabricating the liner comprises: applying an alignment indicator to the liner in such a way that the user can align the alignment indicator when worn to an anterior longitudinal midline of the limb, wherein the alignment indicator represents zero degrees, wherein the plurality of enhanced compression areas number four and are circumferentially located at 45, 135, 225, and 315 degrees relative to the alignment indicator.

A second method for attaching shims to a liner such as the liner fabricated according to the exemplary method described above comprises: selecting a first shim; selecting a second shim, wherein the first shim has a first thickness, wherein the second shim has a second thickness; attaching the first shim to a first attachment area chosen from the at least three attachment areas; attaching the second shim to a second attachment area chosen from the at least three attachment areas; and repeating the above steps with additional shims and the remainder of the attachment areas as necessary to prevent substantial movement of a skeletal structure within the limb when the liner is worn with the socket, wherein the first thickness, the second thickness, and the thickness of additional shims are selected in such a way as to prevent substantial movement of the skeletal structure within the limb when the liner is worn with the socket.

If the shim durometers allow it, the user may attach the shims before donning a socket or after donning a socket.

It will be apparent to those skilled in the art that changes and modifications may be made in the embodiments illustrated and described, without departing from the spirit and the scope of the invention. Thus, the invention is not to be limited to the particular forms herein shown and described except insofar as indicated by the scope of the appended claim.

What is claimed is:

1. A liner system for reducing motion of a bone within a limb, the bone being surrounded by soft tissue, the system comprising:
   a socket adapted to be worn over the limb;
   a liner adapted to be worn over the limb and under the socket,
   wherein the liner further comprises:
      a longitudinal dimension extending from a distal end to a proximal end of the liner;
      a plurality of alternating compression areas and low compression relief areas circumferentially located around the liner and lying along the longitudinal dimension,
      wherein each compression area has a length that runs along a length of the bone within the limb when worn on the limb;
      wherein each compression area has a centerline substantially parallel to the longitudinal dimension,
      wherein the plurality of compression areas comprise four longitudinally-shaped compression areas having centerlines that are approximately equally spaced and circumferentially located around the liner,
      wherein a maximum radial thickness of the liner at each compression area is thicker than a minimum radial thickness of the liner at each low compression relief area;
      wherein the maximum radial thickness of each compression area is sized and dimensioned to apply a greater compression force on the soft tissue than the low compression relief areas when the liner is worn on the limb and under the socket; and
      wherein the maximum radial thickness of each compression area is sized and dimensioned to impede further motion of the bone toward a wall of the socket when the liner is worn on the limb and under the socket by compressing soft tissue against the bone.

2. The liner system of claim 1, wherein the distal end is closed.

3. The liner system of claim 2, wherein the closed distal end is made of a rigid material.

4. The liner system of claim 1, wherein at least one of the compression areas further comprises a gel.

5. The liner system of claim 4, wherein the gel is selected from the group consisting of a shear-thinning gel, a shear-thickening gel, a magneto rheological gel, an electrorheological gel, and a thermoresponsive gel.

6. The liner system of claim 1, wherein a gel is embedded in at least one of the compression areas.

7. The liner system of claim 6, wherein the gel is selected from the group consisting of a shear-thinning gel, a shear-thickening gel, a magneto rheological gel, an electrorheological gel, and a thermoresponsive gel.

8. The liner system of claim 1, wherein the plurality of compression areas comprise a plurality of attachment areas and a plurality of shims that removably couple with the plurality of attachment areas.

9. The liner system of claim 8, wherein at least one of the attachment areas is in a discontinuous configuration.

10. The liner system of claim 1, wherein at least one of the compression areas comprises a removable shim.

11. The liner system of claim 10, wherein the liner is integrally formed by at least one of the following: casting, injection molding, extrusion molding, thermoforming, and rotational molding.

12. The liner system of claim 10, wherein the shim is at least approximately 0.4 mm greater than a minimum radial thickness of the liner.

13. The liner system of claim 12, wherein the shim comprises a gel.

14. The liner system of claim 13, wherein the gel is selected from the group consisting of a shear-thinning gel, a shear-thickening gel, a magneto rheological gel, an electrorheological gel, and a thermoresponsive gel.

15. The liner system of claim 12, wherein the shim has a maximum durometer adapted to permit a user to don and doff the liner while the shim is attached to the liner.

16. The liner system of claim 10, wherein the shim is at least approximately 0.8 mm thick.

17. The liner system of claim 10, wherein the shim is selectable from a kit of component parts comprised of a variety of customizable shims.

18. The liner system of claim 1, wherein the liner is integrally formed by at least one of the following: casting, injection molding, extrusion molding, thermoforming, and rotational molding.

19. The liner system of claim 18, wherein a gel is embedded in at least one of the compression areas.

20. The liner system of claim 19, wherein the gel is selected from the group consisting of a shear-thinning gel, a shear-thickening gel, a magneto rheological gel, an electrorheological gel, and a thermoresponsive gel.

21. The liner system of claim 1, wherein one or more of the plurality of compression areas comprises a pocket.

22. The liner system of claim 1, wherein the shim is selectable from a kit of component parts comprised of a variety of formable shims.

23. A liner system for a limb comprising a bone surrounded by soft tissue, the system comprising:
   a socket adapted to be worn over the limb;
   a liner adapted to be worn over the limb and under the socket,
   wherein the liner further comprises:
      a longitudinal dimension extending from a distal end to a proximal end of the liner;
      a plurality of alternating attachment areas and relief areas circumferentially located around the liner and lying along the longitudinal dimension,
      wherein each attachment area has a centerline substantially parallel to the longitudinal dimension, wherein the plurality of attachment areas comprise four longitudinally-shaped compression areas having centerlines that are approximately equally spaced and circumferentially located around the liner, wherein the liner at the attachment areas further comprises a fastener or pocket for attaching a shim, wherein a broadest width of each attachment area is narrower than the longitudinal dimension, wherein each attachment area is adapted to extend at least approximately 10% the longitudinal dimension;

wherein a maximum radial thickness of the shim is sized and dimensioned to apply a greater compression force on the soft tissue than the relief areas when the liner is worn on the limb with a socket; and wherein the maximum radial thickness of each compression area is sized and dimensioned to impede further motion of the bone towards a wall of the socket when the liner and socket are worn on the limb by compressing soft tissue against the bone.

24. The liner system of claim 23, wherein at least one of the attachment areas is in a discontinuous configuration.

25. The liner system of claim 23, further comprising the shim.

26. The liner system of claim 25, wherein the shim is at least approximately 0.8 mm thick.

27. The liner system of claim 25, wherein the shim is selectable from a kit of component parts comprised of a variety of customizable shims.

28. The liner system of claim 25, wherein the shim comprises a gel.

29. The liner system of claim 28, wherein the gel is selected from the group consisting of a shear-thinning gel, a shear-thickening gel, a magneto rheological gel, an electrorheological gel, and a thermoresponsive gel.

30. The liner system of claim 25, wherein the shim has a maximum durometer adapted to permit a user to don and doff the liner while the shim is attached to the liner.

31. The liner system of claim 25, wherein the shim is selectable from a kit of component parts comprised of a variety of formable shims.

32. The liner system of claim 23, wherein the distal end is closed.

33. The liner system of claim 32, wherein the closed distal end is made of a rigid material.

34. The liner system of claim 23, wherein at least one of the attachment areas further comprises a gel.

35. The liner system of claim 34, wherein the gel is selected from the group consisting of a shear-thinning gel, a shear-thickening gel, a magneto rheological gel, an electrorheological gel, and a thermoresponsive gel.

* * * * *